(12) United States Patent
Tsuzuki et al.

(10) Patent No.: US 8,702,934 B2
(45) Date of Patent: Apr. 22, 2014

(54) GAS SENSOR

(75) Inventors: Masao Tsuzuki, Kakamigahara (JP);
Tomohiro Tajima, Kasugai (JP);
Tomoki Fujii, Kani (JP); Hisaharu Nishio, Tokai (JP); Takaya Yoshikawa, Kasugai (JP); Kunihiko Yonezu, Kuwana (JP)

(73) Assignee: NGK Spark Plug Co., Ltd., Aichi (JP)

( * ) Notice: Subject to any disclaimer, the term of this patent is extended or adjusted under 35 U.S.C. 154(b) by 206 days.

(21) Appl. No.: 13/008,294

(22) Filed: Jan. 18, 2011

(65) Prior Publication Data

US 2011/0174617 A1 Jul. 21, 2011

(30) Foreign Application Priority Data

Jan. 18, 2010 (JP) .................................. 2010-008503

(51) Int. Cl.
*G01N 27/407* (2006.01)

(52) U.S. Cl.
USPC ........... 204/406; 204/411; 204/412; 204/424; 204/431; 205/784; 205/784.5; 73/23.31; 73/23.32; 123/703

(58) Field of Classification Search
USPC ......... 204/400–401, 404, 406–412, 415–416, 204/421–433; 205/775.5, 782–788; 73/23.31, 23.32; 123/672–703
See application file for complete search history.

(56) References Cited

U.S. PATENT DOCUMENTS

| 5,747,669 | A | * | 5/1998 | Suzuki | .......................... 73/23.21 |
| 7,222,516 | B2 | | 5/2007 | Nishio et al. | |
| 2006/0243028 | A1 | * | 11/2006 | Nishio et al. | ................. 73/31.05 |
| 2009/0200164 | A1 | | 8/2009 | Yoshikawa et al. | |

FOREIGN PATENT DOCUMENTS

| JP | 2005-10156 | A | | 1/2005 |
| JP | 2005-201888 | A | | 7/2005 |
| JP | 2007-47075 | A | | 2/2007 |
| JP | 2007071582 | A | * | 3/2007 |
| JP | 2007-121118 | A | | 5/2007 |
| JP | 2008-39568 | A | | 2/2008 |
| JP | 2008-170398 | A | | 7/2008 |
| JP | 2008-268152 | A | | 11/2008 |
| JP | 2009-186424 | A | | 8/2009 |

OTHER PUBLICATIONS

Nakamura et al., JP200771582A english equiv of abstract, 2007.*
Communication dated Dec. 25, 2012 from the Japanese Patent Office in counterpart Japanese application No. 2010-008503.

* cited by examiner

*Primary Examiner* — Susan D Leong
(74) *Attorney, Agent, or Firm* — Sughrue Mion, PLLC

(57) ABSTRACT

A gas sensor including a gas sensor element that extends in an axial direction and has a detection section at a front-end side thereof, and an electrode pad at a rear-end side thereof; a connection terminal that is electrically connected to the electrode pad; and an insulated separator that extends along the axial direction and has an inserting hole into which the connection terminal is inserted. An element side section is arranged within the inserting hole and is connected the electrode pad, and an external circuit side section extends further to the outside in a diametrical direction than an outer surface of the separator through one or more first bending sections from the element side section.

7 Claims, 9 Drawing Sheets

FIG. 8A
FIG. 8B
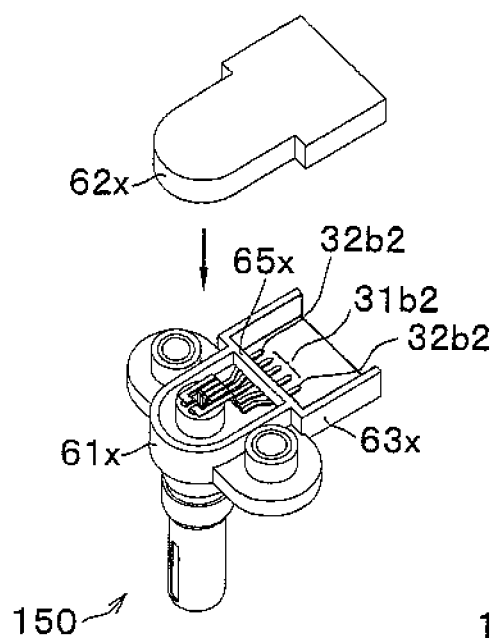
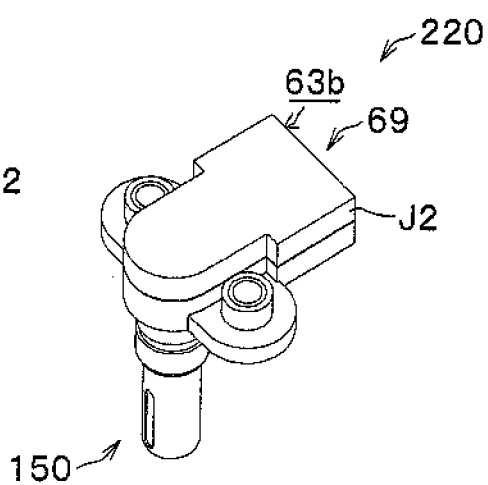

GAS SENSOR

BACKGROUND OF THE INVENTION

1. Field of the Invention

The present invention relates to a gas sensor including a gas sensor element that detects the concentration of a gas to be measured.

2. Description of the Related Art

A gas sensor is attached to an intake air system (for example, an intake air pipe or an intake air manifold) of an internal combustion engine such as a diesel engine, a gasoline engine or the like, and a specific gas concentration is monitored so that the combustion state or the like is controlled. A structure of such a gas sensor is described in Patent Document 1. However, in the gas sensor that is attached to the intake air system of the internal combustion engine, since the attachment is restricted by a structure or a layout in a vicinity of the intake air pipe, an axis of the gas sensor itself is inclined and attached to an axis of the intake air pipe. The gas sensor is fixed to the intake air pipe such that a male threaded section provided at the outside of a case (a metal shell) accommodating the gas detection element therein is tightened into a female threaded section that is incorporated into a wall surface of the intake air pipe.

When a vehicle having mounted therein the internal combustion engine is subjected to impact, secure clearance between the hood and the engine components is required for improving safety. In this regard, there is a need to shorten the projection length of the gas sensor projecting towards the outside of the intake air pipe.

[Patent Document 1] Japanese Patent Application Laid-Open No. 2008-268152-A

3. Problems to be Solved by the Invention

Since the above-described known gas sensor is attached to the intake air pipe using the male threaded section of the case, if the axis of the male threaded section of the case and the axis of the female threaded section of the intake air pipe are inclined, an attachment angle of the gas sensor can be changed with respect to the intake air pipe. However, the depth of attachment of the gas sensor is difficult to change, and the extent to which the projection length that the gas sensor projects towards the outside of the intake air pipe can be shortened is limited.

SUMMARY OF THE INVENTION

It is therefore an object of the invention to provide a gas sensor in which the height of the gas sensor in the axial direction is lowered so that the projection length can be shortened when the gas sensor is mounted to an attachment object body such as an air intake pipe.

The above object has been achieved by providing, in a first aspect (1) of the invention, a gas sensor comprising: a gas sensor element that extends in an axial direction and has a detection section that detects a specific gas component in a measured gas at a front-end side thereof, and an electrode pad at a rear-end side thereof; a connection terminal that is electrically connected to the electrode pad; and an insulated separator that extends along the axial direction and has an inserting hole into which the connection terminal is inserted, wherein the connection terminal has an element side section that is arranged within the inserting hole and connects to the electrode pad, and an external circuit side section that extends further to the outside in a diametrical direction than an outer surface of the separator through one or more first bending sections from the element side section.

According to the above aspect (1), since the external circuit side sections extends to the outside in the diametrical direction further than the outer surface of the separator, the respective heights of the external circuit side sections are lowered. Also, read wire connected to the connector terminal is arranged on rear side not further than the upper surface of the separator so that the height of the gas sensor in the axial direction can be lowered by the same amount, and so that the projection length can be shortened when the gas sensor is attached to the attachment object body.

Also, the separator may be a cylindrical member that surrounds the entire periphery of the inserting hole and may also have a shape in which a portion of the cylindrical member is cut-out so as to expose a portion of the inserting hole to the outside.

Also, the element side section may be arranged within the inserting hole of the separator, and may be, for example, a rod shape member that extends in a straight line in the axial direction, or a U-shaped member that is bent and extends within the inserting hole of the separator.

Also, "the external circuit side section extends further to the outside in a diametrical direction than the outer surface of the separator" is determined when the separator is viewed in the axial direction from the rear side (or the front side) of the separator.

Also, the end section that is opposite the element side section of the external circuit side section may be directly connected to an external circuit, or may be connected to the external circuit through another terminal or a lead wire.

Furthermore, when the gas sensor attaches to the attachment object body, if the clearance between the bonnet of the vehicle and the external circuit side section is sufficiently secured, the end section that is opposite the element side section may be extended further to rear-end side of the gas sensor in the axial direction and may also be extended to the front-end side.

In a preferred embodiment (2) of the gas sensor (1) of the present invention, the gas sensor includes a cover that covers the separator, wherein the cover has a connector section that has an opening that is capable of connecting in the diametrical direction, and the connector section is an integral part of the cover.

According to the above embodiment, the connector section that electrically connects an external circuit and the gas sensor element is an integral part of the gas sensor. In this manner, the gas sensor can be made compact, and the reliability of the electric connection can be enhanced as compared to a configuration in which the connector section is fashioned separate from the gas sensor, and further, the gas sensor and the connector section are connected through the external circuit side section to an external current, either directly or through another terminal or a lead wire.

Thus, in a case where the connector section is integrally formed with the gas sensor, if the opening of the connector section is capable of connecting in the diametrical direction, the height of the gas sensor in axial direction can be suppressed and the projection length can be shortened when the gas sensor is attached to the attachment object body.

In another preferred embodiment (3) of the gas sensor (1) of the present invention, the external circuit side section integrally has a first terminal section that extends to the center side of the separator in the axial direction through a second bending section that is arranged further to the outside in the diametrical direction than the outer surface of the separator, and a second terminal section that extends to the outside in the diametrical direction through a third bending section from the first terminal section, and wherein the second terminal section is inserted through the opening of the connector section.

According to the above embodiment, the second terminal section extends to the outside in the diametrical direction through the first terminal section that extends to center side of the separator in the axial direction. In this manner, the position of the second terminal section can be arranged in the vicinity of the center of the separator in the axial direction. Generally, the connector wall that forms the opening of the connector section is formed in the periphery of the second terminal section which is inserted to the connector section. At this time, the second terminal section is positioned so that the height of the rear-end wall of the connector wall is lowered, the height of the gas sensor in the axial direction is lowered by the same amount, and the projection length is thereby shortened when the gas sensor is attached to the attachment object. Also, the second terminal section is positioned so that the front-end wall of the connector section does not interfere with the attachment object of the gas sensor. As a result, a narrowing in the depth of the attachment can be prevented, and similarly the projection length of the gas sensor can be shortened.

Also, the external circuit side section is directly inserted through the opening of the connector section so that the reliability of the electrical connection can be enhanced.

In yet another preferred embodiment (4) of the gas sensor (1) of the present invention, the external circuit side section integrally has a first terminal section that extends to the center side of the separator in the axial direction through a second bending section that is arranged further to the outside in the diametrical direction than the outer surface of the separator, and a second terminal section that extends to the outside in the diametrical direction through a third bending section from the first terminal section, and wherein the second terminal section is electrically connected to a connector terminal that is inserted through the opening of the connector section in the diametrical direction.

According to the above embodiment, the second terminal section extends to the outside in the diametrical direction through the first terminal section that extends to a center side of the separator in the axial direction. In this manner, the position of the connector terminal that is connected to the second terminal section can be arranged in the vicinity of the center of the separator in the axial direction. Generally, the connector wall that forms the opening of the connector section is formed in the periphery of the connector terminal which is inserted to the connector section. At this time, the connector terminal is positioned so that the height of the rear-end wall of the connector wall is lowered, the height of the gas sensor in the axial direction is lowered by the same amount, and the projection length is thereby shortened when the gas sensor is attached to the attachment object. Also, the second terminal section is positioned so that the front-end wall of the connector section does not interfere with the attachment object of the gas sensor. As a result, a narrowing in the depth of the attachment can be prevented, and similarly the projection length of the gas sensor can be shortened.

In yet another preferred embodiment (5) of the gas sensor (1) of the present invention, a connector terminal is inserted through the opening of the connector section, the connector terminal includes a first connector terminal section that is inserted through the opening of the connector section in the diametrical direction, and a second connector terminal section that extends to the front-end side and/or the rear-end side of the separator in the axial direction through a fourth bending section from the first connector terminal section, and the second connector terminal section is electrically connected to the external circuit side section.

According to the above embodiment, the second connection terminal section that extends to the front-end side and/or the rear-end side of the separator in the axial direction is included in the connection terminal. Also, the second connector terminal section is electrically connected to the external circuit side section so that the position of the first connection terminal section that is inserted through the opening of the connector section can be arranged in the vicinity of the center of the separator in the axial direction. Generally, the connector wall that forms the opening of the connector section is formed in the periphery of the first connector terminal section which is inserted to the connector section. At this time, the first connector terminal is positioned so that the height of the rear-end wall of the connector wall is lowered, the height of the gas sensor in the axial direction is lowered by the same amount, and the projection length is thereby shortened when the gas sensor is attached to the attachment object. Also, the first connector terminal section is positioned so that the front-end wall of the connector section does not interfere with the attachment object of the gas sensor. As a result, a narrowing in the depth of the attachment can be prevented, and similarly the projection length of the gas sensor can be shortened.

Furthermore, since the second connector terminal section is mounted at the connector terminal that is relatively thick and has high stiffness. Thus, when the second connector terminal section is connected to the external circuit side section, an elastic force of the second connector terminal section is also increased and a press contact of both is increased by the elastic force so that the reliability of the electrical connection is enhanced.

In yet another preferred embodiment (6) of the gas sensor of any of (1) to (5) of the present invention, the rear-end side of the gas sensor element is inserted within the inserting hole of the separator, and the element side section of the connection terminal is slidably connected to the electrode pad of the gas sensor element that is accommodated in the inserting hole.

According to the above embodiment, the gas sensor element (or the separator) can be accommodated beforehand in the cover and after that, the separator (or the gas sensor element) can be fitted and then the gas sensor can be easily manufactured.

In yet another preferred embodiment (7) of the gas sensor (2) of the present invention, the gas sensor element has a rectangular shape, wherein the electrode pads are arranged on a first surface of the gas sensor element that faces the connector section and on a second surface of the gas sensor element that is opposite the first surface, and the external circuit side section of the connection terminal that is connected to the electrode pad formed on the second surface is arranged further outside of the connector section in the diametrical direction than the external circuit side section of the connection terminal that is connected to the electrode pad that is formed on the first surface.

Thus, even in a case where a plurality of connection terminals is used, a break of the external circuit side sections among one another can be prevented, a suitable connection type can be employed, and the height of the gas sensor in axial direction can be lowered.

In yet another preferred embodiment (8) of the gas sensor (2) of the present invention, the gas sensor element has a rectangular shape, the electrode pads are arranged on a first surface of the gas sensor element that faces the connector section and on a second surface of the gas sensor element that is opposite the first surface, one of the external circuit side section of the connection terminal that is connected to the electrode pad formed on the second surface and the external circuit side section of the connection terminal that is connected to the electrode pad formed on the first surface is arranged to the rear of the separator and the other is arranged to the front of the separator.

Thus, a break of the external circuit side sections among one another can be prevented, a suitable connection type can be employed, and the height of the gas sensor in the axial direction can be lowered.

BRIEF DESCRIPTION OF THE DRAWINGS

Illustrative aspects of the invention will be described in detail with reference to the drawings wherein:

FIGS. 8A and 8B are perspective views illustrating a configuration of a gas sensor according to a third embodiment of the invention.

DETAILED DESCRIPTION OF THE PREFERRED EMBODIMENTS

Hereinafter, the invention will be described in greater detail with reference to the drawings. However, the present invention should not be construed as being limited thereto.

Figure 1:
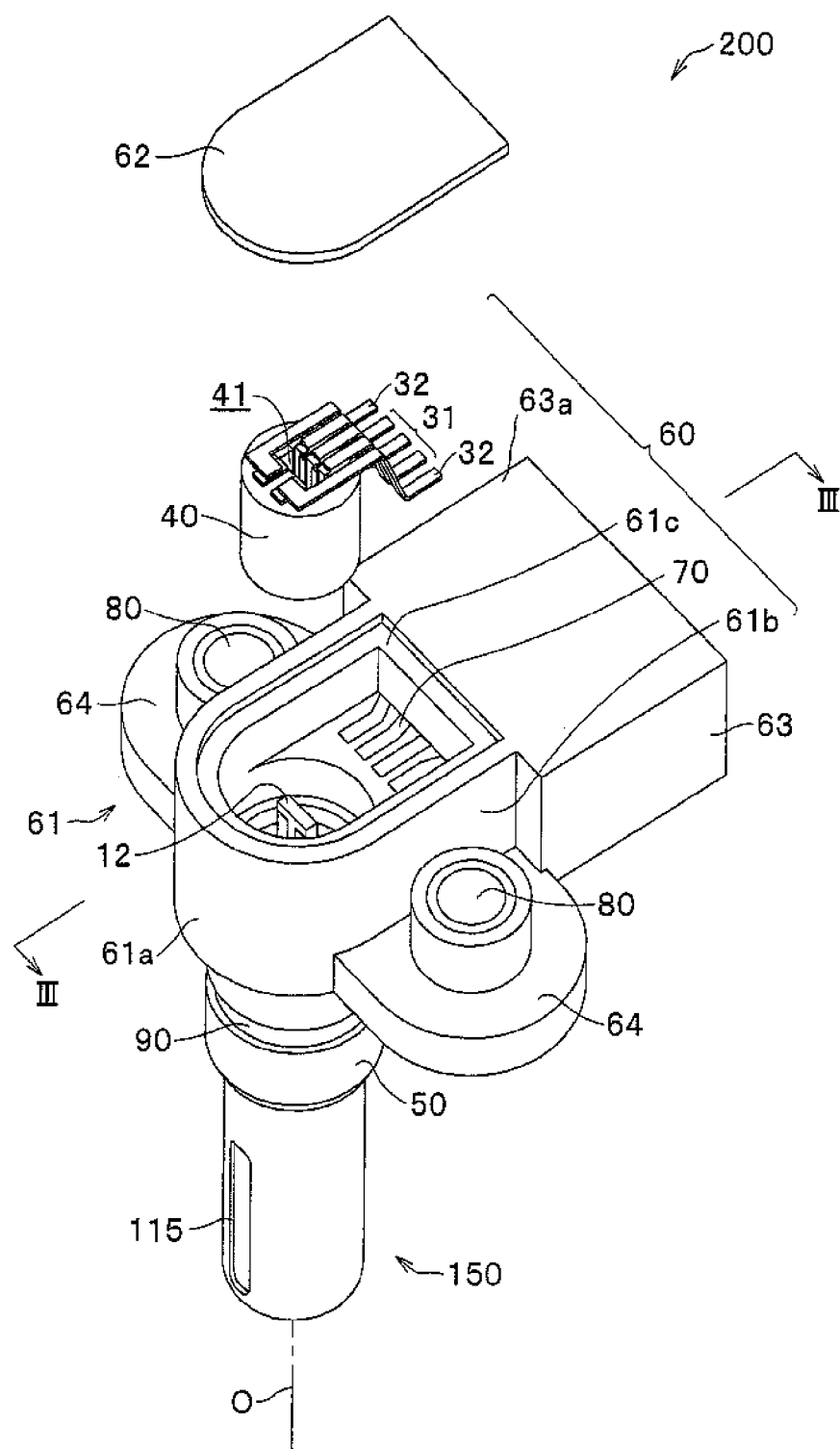
FIG. 1 is a perspective view illustrating a configuration of a gas sensor according to a first embodiment of the invention.
Figure 2:
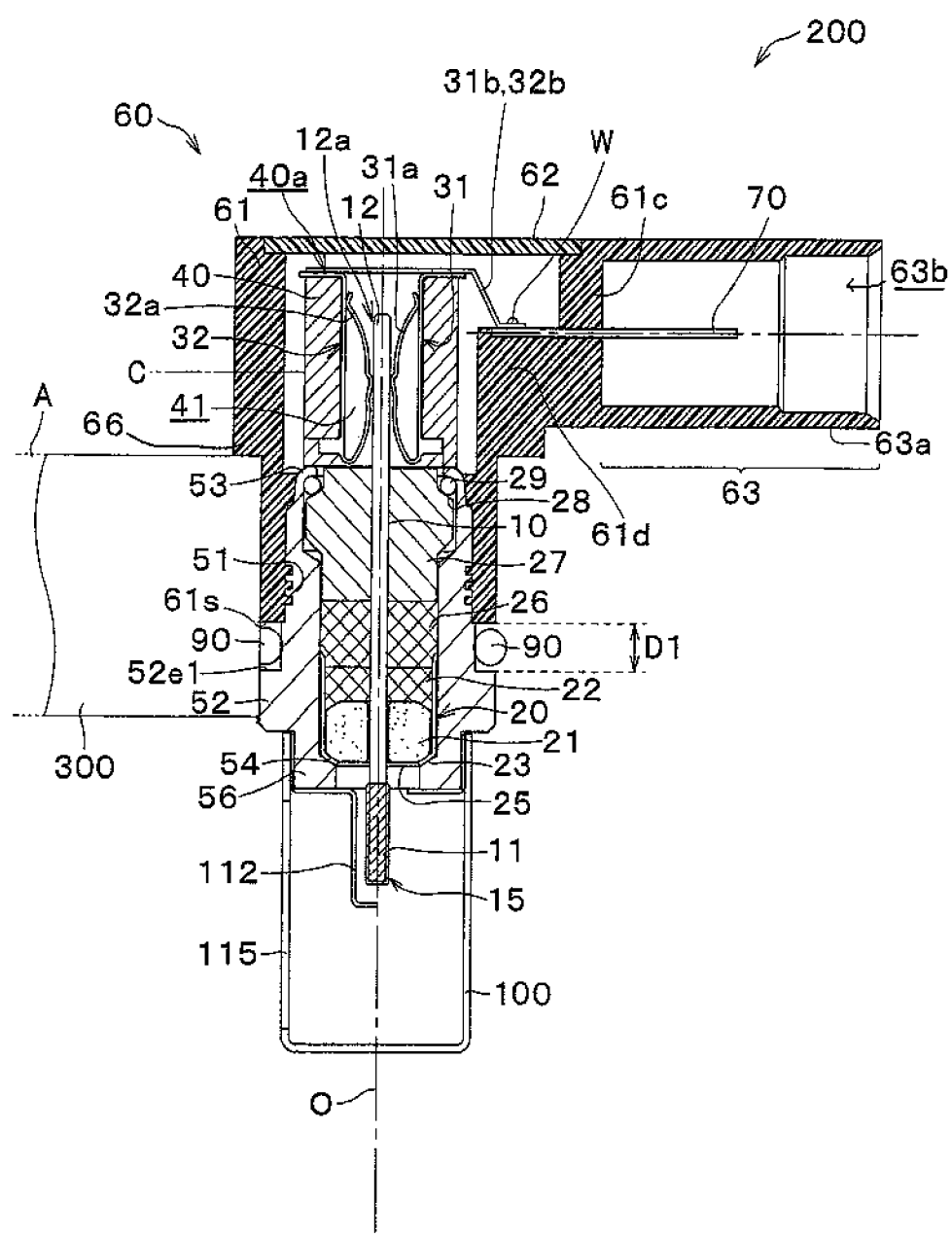
FIG. 2 is a cross sectional view along a line III-III in FIG. 1.

FIG. 1 is a perspective view illustrating a configuration of a gas sensor 200 according to a first embodiment, and FIG. 2 is a cross sectional view along a line III-III in FIG. 1.

The gas sensor 200 includes an element assembly 150 (including the gas sensor element 10), a resin cover 60 that is fixed the element assembly 150, a ceramic separator 40 that is accommodated within the cover 60, and connection terminals 31 and 32 attached to the separator 40. Also, in this embodiment, the cover 60 is configured as a cover main body 61 that is insert molded and fixed to the element assembly 150, and a lid 62 that covers the cover main body 61 from the rear side and closes an interior space of the cover main body 61. Also, a seal member (O-ring) 90, described below, is fitted to the outside between a metal shell 50 of the element assembly 150 and the cover main body 61.

Figure 3:
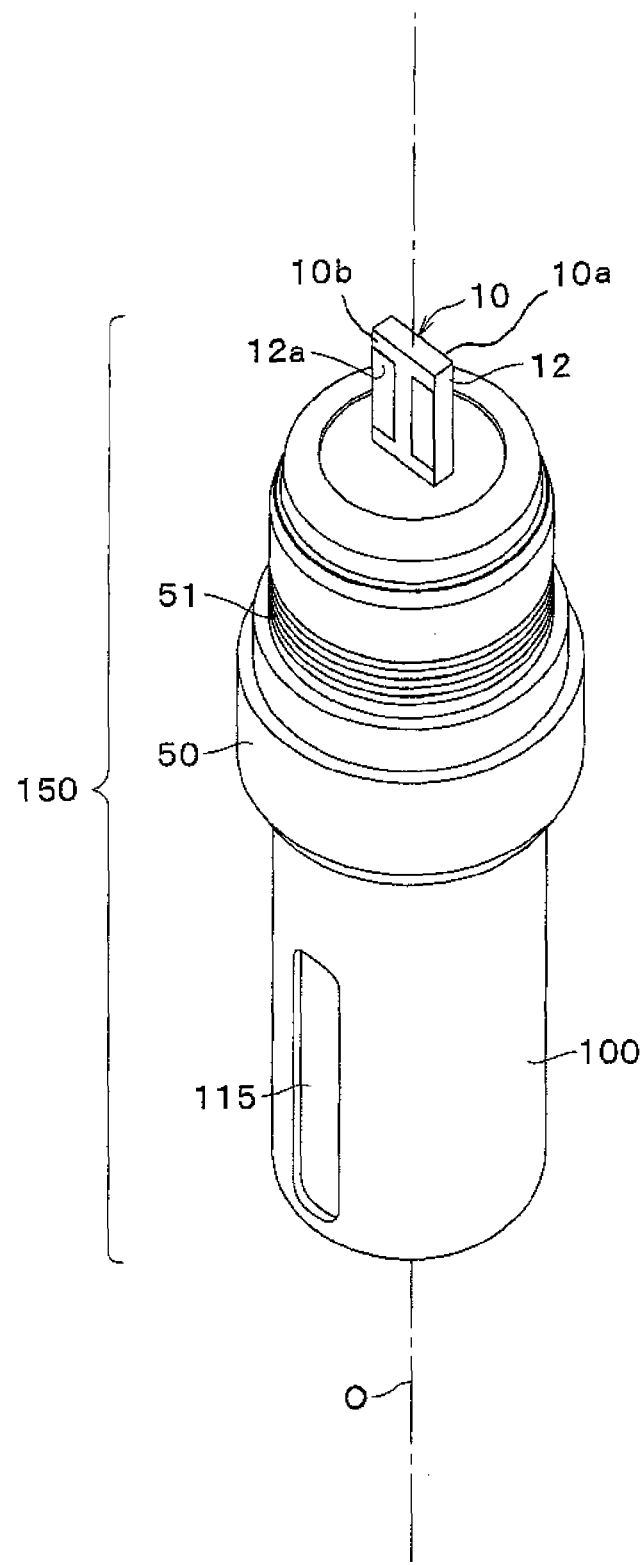
FIG. 3 is a perspective view of a gas sensor element that is held within the gas sensor.

The element assembly 150 will be described with reference to FIGS. 2 and 3. FIG. 3 is a perspective view of an element assembly 150 that is held within the gas sensor according to the first embodiment of the invention. In FIG. 3, the axial direction O (shown as a dashed-dot line) of the gas sensor element 10 is illustrated in an up and down direction. A rear-end section 12 is a rear-end section of the gas sensor element 10 (and also the gas sensor), and a detection section 11 (see FIG. 2) side of the gas sensor element 10 opposite the rear-end section 12 is a front-end side of the gas sensor element 10 (and also the gas sensor). A direction orthogonal to the axial direction O is referred to herein as the "diametrical direction".

In the description "front-end of a terminal" of the connection terminal and the connector terminal described below, the terminal front-end is referred to as the end section of the terminal. The terminal front-end is different from the "front-end" that is seen from the axial direction O of the gas sensor element 10, and has no relation with the axial direction O.

The gas sensor element 10 has a substantially rectangular columnar shape that extends in the axial direction O as known in the art. The gas sensor element 10 is a laminated body in which a detection element that detects oxygen concentration and a heater that heats the detection element so as to quickly activate the detection element are bonded together. The detection element is configured as a solid electrolyte body comprising zirconium as a main component and a pair of electrodes comprising platinum as a main component. The detection element also laminates the solid electrolyte body and pair of electrodes via an insulation layer in which a hollow measurement chamber is formed at a portion thereof. More specifically, the detection element has an oxygen pump cell and an oxygen concentration measurement cell. In the oxygen pump cell, one of the pair of electrodes formed on opposing sides of the solid electrolyte body is exposed to the outside, and the other electrode is arranged so as to be exposed to the measurement chamber. In the oxygen concentration measurement cell, one of the pair of electrodes formed on opposing surfaces of the solid electrolyte body is opposed to the measurement chamber, and the other electrode forms a reference gas chamber.

A current that flows between the pair of electrodes of the oxygen pump cell is controlled so that an output voltage of the oxygen concentration measurement cell assumes a predetermined value. Oxygen within the measurement chamber is pumped out or oxygen is pumped into the measurement chamber from the outside.

A detection section 11 in which current flows depending on the oxygen concentration is configured of a portion that is sandwiched by the pair of electrodes of the oxygen pump cell and the electrodes of the solid electrolyte body. Also, at the rear-end section 12 of the gas sensor element 10, five electrode pads 12a (two of the five are illustrated in a second surface 10b side of the gas sensor element 10 and the remaining three are illustrated in a first surface 10a in FIG. 1) are formed so as to take out an output signal from the detection element or to supply power from a power-supply to the heater.

As shown in FIG. 2, in the front-end side slightly off center in the axial direction of the gas sensor element 10, a metal cup 20 is arranged in a state where the gas sensor element 10 passes through an interior thereof and the detection section 11 projects from a opening 25 in a bottom of a barrel. The metal cup 20 is a member for holding the gas sensor element 10 within the metal shell 50, and a front-end side peripheral section 23 in a bottom of a barrel is formed in a taper shape toward an outer periphery surface. A ceramic ring 21 made of aluminum and a talc ring 22 solidified by pressing talc powder are accommodated within the metal cup 20 in a state where the gas sensor element 10 passes therethrough. The talc ring 22 is pressed within the metal cup 20 and charged. Thus, the gas sensor element 10 is positioned and held within the metal cup 20.

The periphery of the gas sensor element 10 integral with the metal cup 20 is surrounded and held by the cylindrical metal shell 50. The metal shell 50 is made of stainless steel such as SUS 430. Specifically, an end section 54 is formed at the inner periphery of the metal shell 50, and a front-end side peripheral section 23 of the metal cup 20 in which the gas sensor element 10 is held is engaged at the end section 54. Further, a talc ring 26 is charged from the rear-end side of the metal cup 20 at the inner periphery of the metal shell 50 in a state where the gas sensor element 10 passes therethrough. Thus, a cylindrical sleeve 27 is inserted within the metal shell 50 so as to press the talc ring 26 from the rear-end side. A step shape shoulder section 28 is formed at the outer periphery of the rear-end side of the sleeve 27, and a circular shape tightening packing 29 is arranged at the shoulder section 28.

Meanwhile, a concave-convex section 51 projecting towards the axial direction O is formed at the outer periphery rear-end side of the metal shell 50 so as to increase contact with a resin cover (described below) by a wedge effect. Further, a large diameter section 52 having a large diameter and a front-end engaging section 56 in which a protector 100 (described below) is engaged are formed to the front of the concave-convex section 51 of the metal shell 50. Meanwhile, a tightening section 53 that is for tightening and holding the gas sensor element 10 within the metal shell 50 is formed at the rear-end side of the concave-convex section 51.

The tightening section 53 of the metal shell 50 is tightened so as to press the shoulder section 28 of the sleeve 27 toward the front-end side through the tightening packing 29. The talc ring 26 that is depressed through the sleeve 27 by forming the tightening section 53 is pressed and charged within the metal shell 50. The metal cup 20 and the gas sensor element 10 are positioned and tightly held within the metal shell 50 by the talc ring 26 and the talc ring 22.

Meanwhile, the outer periphery of the detection section 11 of the gas sensor element 10 is covered by a porous protection layer 15, so as to protect the electrode of the detection section 11 that is exposed to the outside from catalyst poisons or water present in the intake air. Thus, the outside protector 100 is attached to the outside of a front-end engaging section 56 of the metal shell, and is fixed by laser welding so that the detection section 11 that is accommodated within the outside protector 100 is protected. An inside protector 112 is arranged between the detection section 11 and the gas inlet hole 115 inside of the outside protector 100, so as to prevent the detection section 11 from being directly exposed to gas that is introduced into the outside protector 100 from the gas inlet hole 115. This configuration prevents moisture or oil entrained in the gas from attaching to the gas sensor element 10, to thereby prevent cracking or breaking of the gas sensor element 10. Also, this configuration prevents smoke that is contained in the gas from attaching to the gas sensor element 10 so as to prevent deterioration of the detection precision of the gas sensor 200.

In a case where the gas sensor 200 is attached to the intake manifold of the internal combustion engine, by aligning the gas inlet hole 115 so as to face the downstream direction of the intake manifold, the generation of cracks or breaks at the gas sensor element 10 and also deterioration in the detection precision of the gas sensor 200 is prevented.

Next, the cover main body 61 will be described with reference to FIGS. 1 and 2. As shown in FIG. 2, the cover main body 61 is insert molded at portions from the concave-convex section 51 of the metal shell 50 to the tightening section 53. Specifically, the cover main body 61 and the metal shell 50 are connected at the concave-convex section 51 having a large surface area so that the contactability and sealing property between the cover main body 61 and the metal shell 50 are enhanced.

In the first embodiment, the outer diameter of the connection section to the metal shell 50 in the cover main body 61 has the same dimension as the outer diameter of the large diameter section 52 of the metal shell 50. Also, the front-end of the cover main body 61 is not formed to the large diameter section 52, and has a clearance with the large diameter section 52 in the axial direction O. Further, the front-end surface of the cover main body 61 forms a step section 61s toward the front-end.

Thus, the seal member (the O-ring) 90 is inserted from outside at a concave recess D1 that is formed between a rear-end surface 52e1 of the large diameter section 52 and the step section (the front end surface) 61s of the cover main body 61, and the seal member (the O-ring) 90 is engaged at the concave recess D1. Also, the rear-end surface 52e1 of the large diameter section 52 has a step section toward the rear-end.

The outer diameter of the seal member 90 is larger than the large diameter section 52, and an opening that is slightly larger than the large diameter section 52 is provided at the attachment object body 300 of the gas sensor. Accordingly, when the gas sensor 200 is inserted and attached to the opening from the front-end side, the seal member 90 is deformed at the wall surface of the attachment object body 300, and a gap between the attachment object body 300 and the metal shell 50 is sealed.

Thus, as shown in FIG. 1, a semi-circular cylindrical section 61a that has a diameter larger than the large diameter section 52 of the metal shell 50 is present to the rear of the connection section to the metal shell 50 of the cover main body 61. Further, two compartment walls 61c extend in parallel opposite the gas inlet hole 115 from an end of the semi-circular cylindrical section 61a. Thus, the ends of both wall sections 61b are closed by a compartment wall 61c that is orthogonal to the surface of wall sections 61b. As described above, the periphery of the rear-end section 12 of the gas sensor element 10 is surrounded by the semi-circular cylindrical section 61a, two wall sections 61b and the compartment wall 61c. The height of the rear-end side of the semi-circular cylindrical section 61a, the two wall sections 61b and the compartment wall 61c is slightly higher than the rear-end section 12 of the gas sensor element 10. Further, the rear-end section 12 (and the separator 40 and a connector terminal 70 described below) is accommodated in the interior space of the cover main body 61.

A semi-circular shape flange section 64 extends outwards of the two surfaces of the wall sections 61b. Each of the flange sections 64 is formed by the insert molding at a metal cylindrical shape collar 80. Thus, a screw is passed through the collar 80 and into a screw hole provided in the attachment object body 300 (for example, the intake manifold of the internal combustion engine) so as to attach the gas sensor 200 to the attachment object. The surfaces toward the front-end of the cover main body 61 and each of the flange sections 64 constitutes the same surface so as to closely contact the outside surface of the attachment object.

Accordingly, when the gas sensor 200 is attached to the attachment object body 300 using each of the flange sections 64, the attachment opening of the attachment object body 300 can be made to have a relatively small diameter. Further, the attachment is easily accomplished compared to the case in which the metal shell 50 is directly screwed shut to the attachment object body 300 regardless of the material of the attachment object body 300.

As shown in FIG. 2, a step section 66 that extends further to the outside in the diametrical direction than the connection section to the metal shell 50 is formed at the semi-circular cylindrical section 61a, and the lower surfaces of each of the flange sections 64 and the step section 66 become an attachment surface A that is connected to the surface of the attachment object body 300.

The cover main body 61 has an opening 63b at a side opposite the gas inlet hole 115 and integrally has a rectangular male type connector section 63 that extends in the diametrical direction (the direction orthogonal to the axial direction O) of the gas sensor 200. A connector wall 63a that forms the opening 63b of the connector section 63 is provided so as to surround the connector terminal 70 and the connector wall 63a is integrally connected to the compartment wall 61c. Thus, the other end of the connector terminal 70 of the connector section 63 is exposed to the interior space from the compartment wall 61c.

The connector section 63 can receive (insert/pull) a counterpart connector (a female connector in the embodiment) in the diametrical direction. The other end of the connector terminal 70 that is exposed to the interior space is outsert molded on a rack section 61d that is extruded from the front-end side to the rear-end side in the interior space of the cover main body 61 and is attached and fixed to the rack section 61d. Also, in the invention, both outsert molding and insert molding can be used to form the cover assembly without particular limitation.

Meanwhile, the rear-end section 12 of the gas sensor element 10 projects beyond the rear of a rear-end (a tightening section 53) of the metal shell 50, and a cylindrical separator 40 made from an insulating ceramic covers the rear-end section 12. An electrode pad 12a provided at the rear-end section 12 of the gas sensor element 10 is accommodated in an inserting hole 41 of the separator 40, and connection terminals 31 and 32 arranged in the inserting hole 41 are electrically connected to the electrode pad 12a. One end (external circuit side sections 31b and 32b described below) of the respective connection terminals 31 and 32 that is exposed to the outside of the separator 40 extends in the diametrical direction and is electrically connected to the connector terminal 70 at spot weld W.

Figure 4:
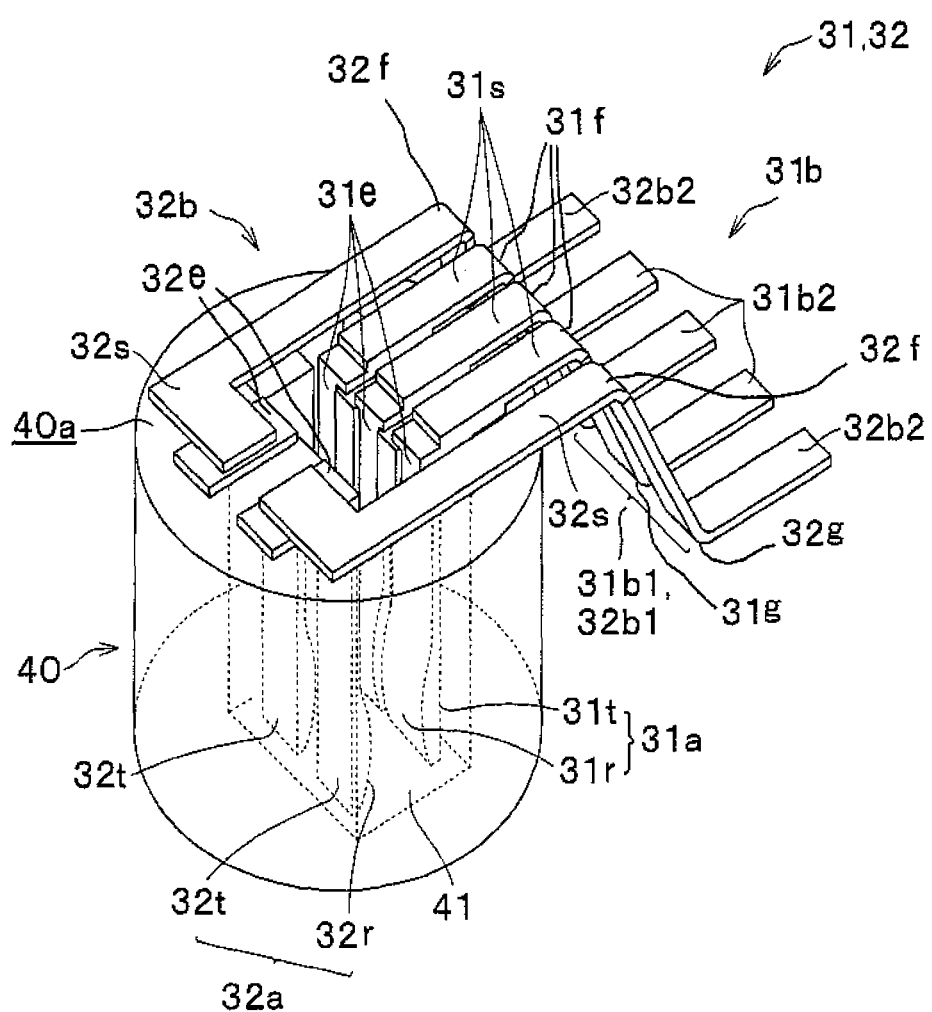
FIG. 4 is a perspective view illustrating a configuration of a connection terminal of the gas sensor according to the first embodiment.

Next, a detailed configuration of the connection terminals 31 and 32 will be given with reference to FIG. 4. FIG. 4 is a perspective view illustrating the separator 40 and the connection terminals 31 and 32. The three connection terminals 31 are lined and arranged on the inner wall surface of the rectangular inserting hole 41 and are connected to three electrode pads 12a respectively, that provide the output of the gas sensor element 10. Meanwhile, two connection terminals 32 are lined and arranged on the surface opposite the connection terminal 31 in the wall surface of the inserting hole 41, and are connected to the two electrode pads 12a that electrically connect to an interior heater of the gas sensor element 10.

The connection terminals 31 and 32 are formed by punching a long piece of a conductive member (a metal piece or the like) with a press or the like, and bending the piece in a predetermined shape. The connection terminals 31 and 32 are arranged within the inserting hole 41 of the separator 40 and integrally have element side sections 31a and 32a that are connected to the electrode pads 12a respectively, and external circuit side sections 31b and 32b which connect the connector terminal 70 and the element side sections 31a and 32a, respectively.

The element side sections 31a and 32a include drawing out sections 31t and 32t that are along the wall surface of the inserting hole 41, and the contact sections 31r and 32r that are bent at the front-end side of the drawing out sections 31t and 32t and expanded to the center of the axial direction of the separator 40 by elastic force. Thus, when the rear-end section 12 of the gas sensor element 10 is inserted into the inserting hole 41 of the separator 40, the element side sections 31a and 32a (the contact sections 31r and 32r) are moved slidably onto respective electrode pads 12a. Further, a press contact of element side sections 31a and 32a to the electrode pad 12a is increased by the elastic force of the element side sections 31a and 32a so that an electrical connection is reliably established.

Next, the external circuit side sections 31b and 32b will be described.

The external circuit side section 31b is integrally formed of horizontal sections 31s that extend in the diametrical direction along the upper surface 40a (the rear-end direction surface 40a) of the separator 40 through a first bending section 31e from a drawing out section 31t, first terminal sections 31b1 that extend from the horizontal section 31s in widening and tilting to the outside in the diametrical direction toward the center in an axial direction from the upper surface 40a of the separator 40 through a second bending section 31f, and second terminal sections 31b2 that horizontally extend to the outside in the diametrical direction through third bending sections 31g from the first terminal sections 31b1.

The external circuit side section 32b is integrally formed of horizontal sections 32s that extend in the diametrical direction along the upper surface 40a of the separator 40 through a first bending section 32e from a drawing out section 32t, first terminal sections 32b1 that extend from the horizontal section 32s in widening and tilting to the outside in the diametrical direction toward the center in an axial direction from the upper surface 40a of the separator 40 through the second bending section 32f, and second terminal sections 32b2 that horizontally extend to the outside in the diametrical direction through third bending sections 32g from the first terminal sections 32b1.

In addition, the angle of the first terminal sections 32b1 is same as the angle of first terminal sections 31b1, and the second terminal sections 32b2 and second terminal sections 31b2 line up with one another.

The horizontal section 31s of the connection terminal 31 is straightly extended from the inserting hole 41 of the separator 40. Meanwhile, left and right horizontal sections 32s of the connection terminal 32 are straightly extended, the same as the horizontal section 31s, from both outsides in the width direction of the three horizontal sections 31s along the outer periphery of the inserting hole 41 so as not to contact the horizontal sections 31s.

As shown in FIGS. 1 and 2, in a state where the electrode pad 12a of the gas sensor element 10 and the connector terminal 70 are electrically connected through the connection terminals 31 and 32, the lid 62 is placed so as to cover the opening in the main body 61 and fixed (for example, by welding), so that the separator 40 is covered by the cover 60 to thereby configure the gas sensor 200.

Next, an example of a method of manufacturing the gas sensor 200 according to the first embodiment of the invention will be described with reference to FIGS. 5A to 5F.

First, the element assembly 150 is prepared by a known method.

Figures 5A, 5B, 5C:
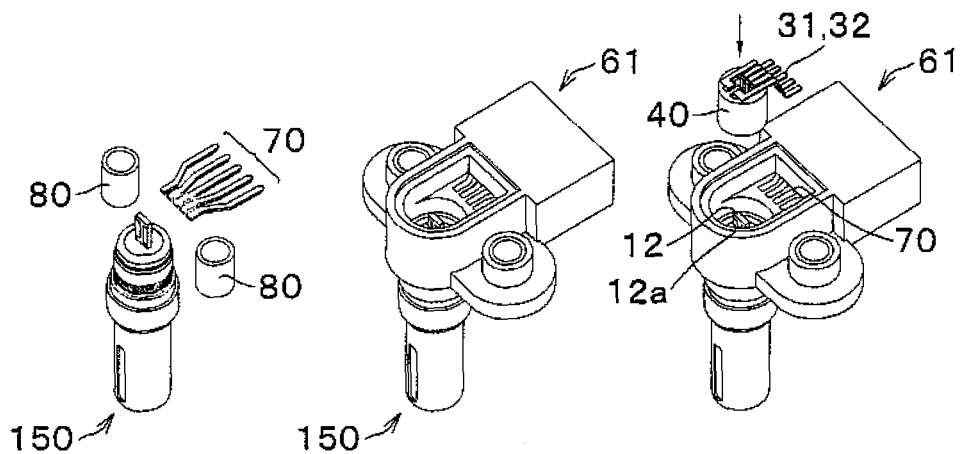
FIGS. 5A to 5F are process drawings illustrating an example of a method of manufacturing the gas sensor according to the first embodiment of the invention.
Figures 5D, 5E, 5F:
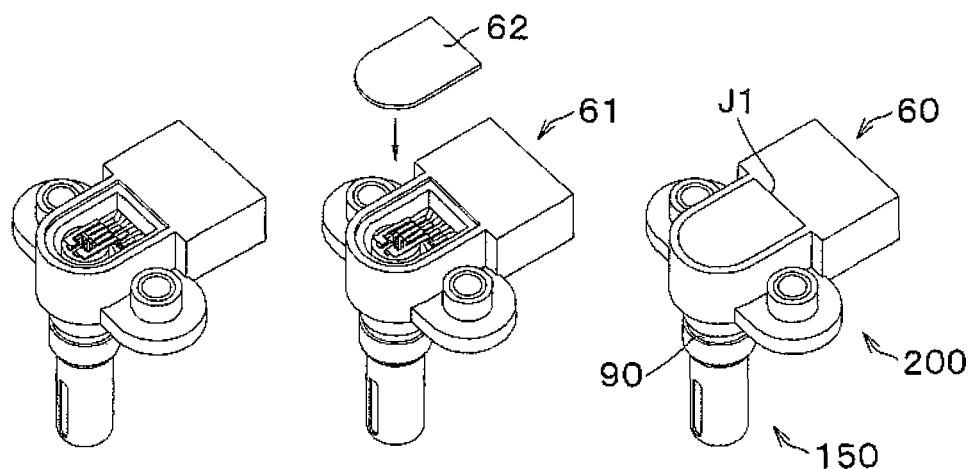

The element assembly 150, the collar 80 and the connector terminal 70 are arranged within a suitable molding (see FIG. 5A). Next, the resin within the molding is formed in an injection mold and the cover main body 61 is insert molded (see FIG. 5B). The separator 40 having the connection terminals 31 and 32 is fitted to the rear-end section 12 of the gas sensor element 20 being arranged within the cover main body 61 (see FIG. 5C). The connection terminals 31 and 32 are connected to the electrode pad 12a and the connector terminal 70 (see FIG. 5D). Also, the connection terminals 31 and 32 and the connector terminal 70 are electrically connected by a technique such as spot welding.

The lid 62 covers the opening of the cover main body 61 (see FIG. 5E), the cover main body 61 and the lid 62 are integrated (for example, by welding) to seal a line J1, and then the cover 60 is formed. Then, the O-ring 90 is inserted from the outside into the concave recess D1 between the large diameter section 52 and the cover main body 61 (neither is shown) to obtain the gas sensor 200 (see FIG. 5F).

As described above, since the external circuit side sections 31b and 32b of the connection terminals 31 and 32 extend to the outside in the diametrical direction than the outside surface of the separator 40, the height of the external circuit side sections 31b and 32b is lowered. Further, the connector terminal 70 is arranged so as not to be to the rear of the upper surface 40a of the separator 40. Consequently, the height of the gas sensor 200 in the axial direction O can be lowered as much (by an amount that the connector 70 might otherwise have been arranged to the rear of the upper surface 40a of the separator 40), and the projection length can be shortened when the gas sensor 200 is attached to the attachment object body 300.

The cover 60 integrally has a connector section 63 that has an opening 63b that can receive (insert/pull) a counterpart connector in the diametrical direction so that the gas sensor 200 may be made compact. Further, the reliability of the electrical connection is enhanced compared to a case where the gas sensor and the connector section are provided separately, and the connector terminal and the connection terminal are electrically connected through a lead wire.

Also, the external circuit side sections 31b and 32b have the first terminal sections 31b1 and 32b1, and the second terminal sections 31b2 and 32b2. In this manner, the position of the connector terminal 70 that is connected to the second terminal sections 31b2 and 32b2 can be arranged in the vicinity of the center of the separator 40 in the axial direction wherein the first terminal sections 31b1 and 32b1 extend to the center of the separator 40 in the axial direction. This is achieved by providing the second bending sections 31f and 32f that are arranged further to the outside in the diametrical direction than the outer surface of the separator 40, and the second terminal sections 31b2 and 32b2 that extend to the outside in the axial direction through the third bending sections 31g and 32g from the first terminal sections 31b1 and 32b1. Thus, the height of the connector wall 63a is also lowered, the height of the gas sensor 200 in the axial direction O can be lowered, and the projection length can be shortened when the gas sensor 200 is attached to the attachment object body 300.

The position of the connector terminal 70 that is connected to the second terminal sections 31b2 and 32b2 can be arranged in the vicinity of the center of the separator 40 in the axial direction. If the connector wall 63a projects to the front-end side further than the attachment surface A, it will interfere with the surface of the attachment object body 300. Specifically, in the embodiment, the connector wall 63a is positioned slightly further to rear-end side than the attachment surface A. As a result, a narrowing of the attachment depth of the gas sensor 200 can be prevented, and the projection length of the gas sensor 200 can be shortened.

Furthermore, the external circuit side section 32b of the connection terminal 32 is arranged further outside of the connector section 63 in the width direction than the external circuit side section 31b of the connection terminal 31. In this manner, the connection terminal 32 is connected to the electrode pad 12a that is formed at the second surface 10b toward a side opposite the connector section 63, and the connection terminal 31 is connected to the electrode pad 12a that is formed at the first surface 10a facing the connector section 63. Thus, even in a case where a plurality of the connection terminals 31 and 32 are used, a break in the external circuit side sections 31b and 32b one upon another can be prevented, a suitable connection shape can employed, and the height of the gas sensor in axial direction can be lowered.

As the attachment object body 300 of the gas sensor 200, various types of internal combustion engines are exemplified, and specifically, the intake air system of the internal combustion engine for vehicles such as automobiles is exemplified. The intake air system is an intake air passage from an intake air opening to the intake air port of the internal combustion engine. For example, an intake air pipe and the intake air manifold that is connected to the intake air port of the internal combustion engine, and that branches from the intake air pipe, are exemplified. The intake air includes not only fresh air (newly entered air that does not include exhaust gas) but also mixed air in which a portion of the exhaust gas is circulated (recirculated) to the intake air system and mixed with fresh air.

The gas sensor element 10 of the above-described embodiment is a so-called full range air-fuel ratio sensor, and may be an oxygen sensor (a λ sensor) and/or an NOx sensor besides the air-fuel ratio sensor.

In a case where a specific gas concentration in the intake air side is detected and then the internal combustion engine is controlled, the internal combustion engine can be controlled more precisely as compared to a case where the gas sensor is mounted at the exhaust gas side and the specific gas concentration at the exhaust gas is then detected. This is because the control according to the specific gas concentration at the intake air side can counteract before combustion (feedforward control), while the control according to the specific gas concentration at the exhaust gas side is a feedback control.

Next, the configuration of the gas sensor 210 according to a second embodiment of the invention will be described with reference to FIGS. 6 and 7. The gas sensor 210 is the same as in the first embodiment, except that the connection terminal 32 of the first embodiment is changed to the connection terminal 33. The same configuration portions as the first embodiment are given the same reference numbers, and thus are not specifically described here.

Figure 6:
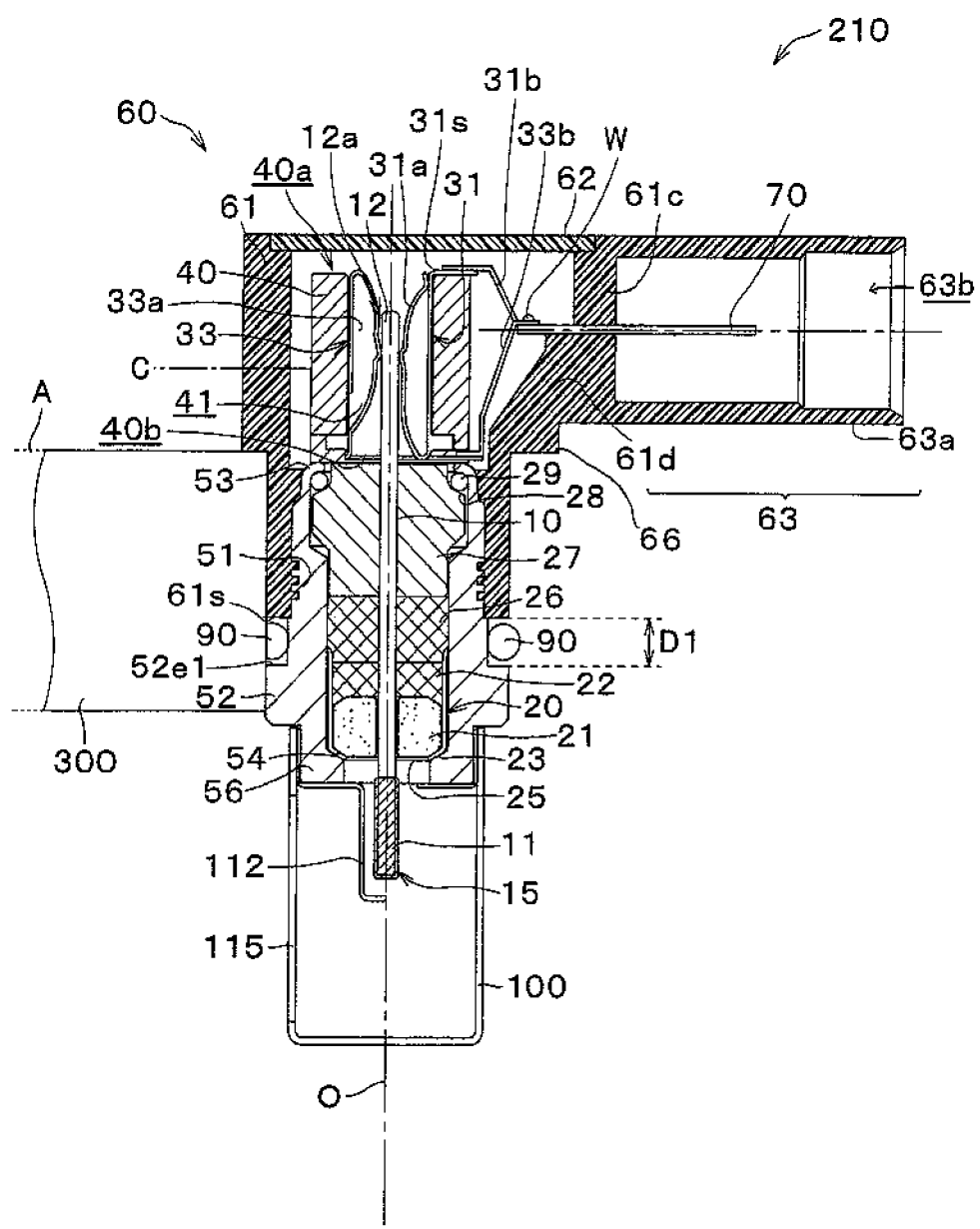
FIG. 6 is a cross sectional view illustrating a gas sensor according to a second embodiment of the invention.

FIG. 6 is a cross sectional view illustrating the gas sensor 210 and is a drawing corresponding to FIG. 3 of the first embodiment. In the drawing, the connection terminal 33 has an element side section 33a and an external circuit side section 33b the same as in the first embodiment. However, the difference from the first embodiment is that the external circuit side section 33b extends further to the outside in the diametrical direction than the outer surface of the separator 40 from the lower surface (the front-end direction) 40b of the separator 40. Since the external circuit side section 33b extends from the lower surface 40b of the separator 40, the wall surface of the rack section 61d is inclined and cut so as not to interfere with the external circuit side section 33b.

Figure 7:
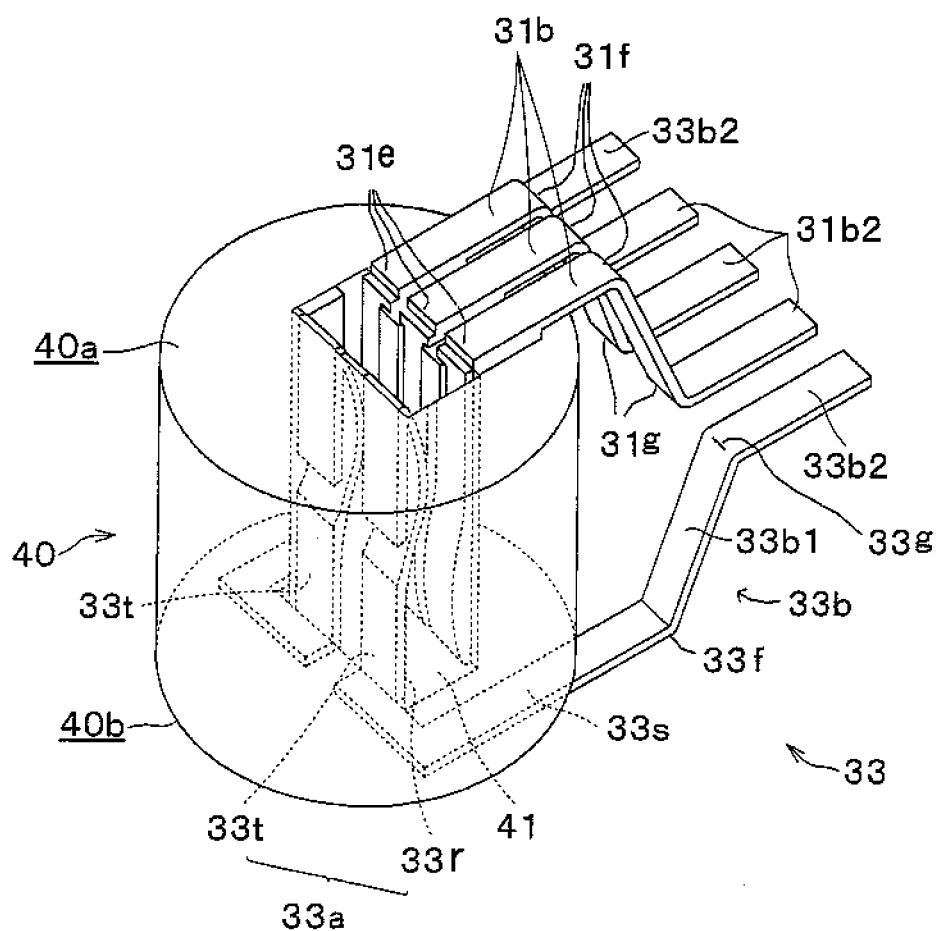
FIG. 7 is a perspective view illustrating a configuration of a connection terminal of the gas sensor according to the second embodiment.

FIG. 7 illustrates a detailed configuration of the connection terminal 33 and corresponds to FIG. 4 of the first embodiment. The configuration of the connection terminal 31 is the same as FIG. 4.

The element side section 33a has a contact section 33r and a take-out section 33t. However, since the external circuit side section 33b is positioned at the lower surface 40b of the separator 40, the take-out section 33t becomes a free end at the front-end side and is bent at the rear-end side. As such, the contact section 33r connected to the rear end side of the take-out section 33t and is connected to a horizontal section 33s of the external circuit side section 33b at the lower surface 40b of the contact section 33r. The horizontal section 33s extends in the diametrical direction along the lower surface 40b of the separator 40 from the take-out section 33t. Also, the same as the horizontal section 32s, the horizontal section 33s is straightly extended along the outer periphery of the inserting hole 41 so as to be positioned at both outsides of the three horizontal sections 31s in the width direction when viewed from the upper surface 40a or the lower surface 40b of the separator 40.

Further, the external circuit side section 33b integrally forms a first terminal section 33b1 that is widened to the outside in the diametrical direction toward the center of the axial direction from the lower surface 40b of the separator 40 through the second bending section 33f from the horizontal section 33s, and a second terminal section 33b2 that extends horizontally to the outside in the diametrical direction through the third bending section 33g from the first terminal section 33b1. The second terminal section 33b2 extends at the same height as the second terminal section 31b2, and the second terminal section 33b2 is arranged in a line with the second terminal section 31b2 even in the second embodiment. Thus, the same as in the first embodiment, when the separator 40 is inserted into the gas sensor element 10, the second terminal section 33b2 and the second terminal section 31b2 contact the connector terminal 70. In the embodiment, the second terminal section 33b2 and the second terminal section 31b2 are electrically connected by welding or the like to a connector terminal 70, respectively.

Even in the second embodiment, since the connection terminals 31 and 33 extend further to the outside in the diametrical direction than the outer surface of the separator 40, the height of the external circuit side sections 31b and 33b is lowered. Also, the connector terminal 70 is arranged so as not to be to the rear of the upper surface 40a of the separator 40. Consequently, the height of the gas sensor in the axial direction O can be lowered as much, and the projection length can be shortened when the gas sensor is attached to the attachment object body 300.

The external circuit side section 33b of the connection terminal 33 is arranged to the front of the lower surface 40b of the separator 40, and the external circuit side section 31b of the connection terminal 31 is arranged to the rear of the upper surface 40a of the separator 40. The connection terminal 33 is connected to the electrode pad 12a that is formed at the second surface 10b on a side opposite the connector section 63, and the connection terminal 31 is connected to the electrode pad 12a that is formed at the first surface 10a facing the connector section 63. Thus, even in a case where a plurality of connection terminals 31 and 33 are used, a break of the external circuit side sections 31b and 33b one upon another can be prevented, a proper connection shape can employed and the height of the gas sensor in axial direction can be lowered.

Next, the configuration of a gas sensor 220 according to a third embodiment of the invention will be described with reference to FIGS. 8A and 8B. The difference from the first embodiment is that the gas sensor 220 has a lower cover 61x and a upper cover 62x which divide the cover 60 into two in the axial direction O instead of a single cover 60 as in the first embodiment. Also, the difference from the first embodiment is that the gas sensor 220 has a configuration such that the second terminal sections 31b2 and 32b2 of the connection terminals 31 and 32 communicate in the opening 63b of the connector section 63 instead of using the connector terminal 70. However, the other configurations are the same as in the first embodiment except for the above-described change, so that the same configuration portions as in the first embodiment are given the same reference numbers and thus are not specifically described here.

FIG. 8 is an exploded perspective view illustrating a configuration of the gas sensor 220 and is a drawing corresponding to FIG. 2 or FIG. 5 of the first embodiment. In the drawing, the configuration of the element side sections 31a and 32a, the horizontal sections 31s and 32s, and the first terminal sections 31b1 and 32b1 of the connection terminals 31 and 32 are the same as in the first embodiment. Meanwhile, the second terminal sections 31b2 and 32b2 extend in the diametrical direction to reach into the connector section 63 through the third bending sections 31g and 32g from the first terminal sections 31b1 and 32b1 respectively.

Thus, the connection terminals 31 and 32 are mounted onto the separator 40 and the lower cover 61x is insert molded the same as in the first embodiment. However, a thickness of the lower cover 61x and the lower connector section 63x that is integral with the lower cover 61x in the axial direction O is about ½ of the cover main body 61 and the connector section 63. The vicinity of center portion in a longitudinal direction of the second terminal sections 31b2 and 32b2 is embedded in a partition wall 65x that is orthogonal to the second terminal sections 31b2 and 32b2 so as to fix the second terminal sections 31b2 and 32b2 to the lower cover 61x.

The upper cover 62x that has the same external shape as the lower cover 61x is mated to the lower cover 61x that is formed as described above from the rear-end side (see FIG. 8A), and the assembly is integrated and sealed at a line J2 to form the cover 69 and thereby obtain the gas sensor 220 (see FIG. 8B).

Even in the third embodiment, since the external circuit side sections 31b and 32b of the connection terminals 31 and 32 extend further to the outside in the diametrical direction than the outside surface of the separator 40, the height of the external circuit side sections 31b and 32b is not high. Consequently, the height of the gas sensor in the axial direction O can be lowered as much, and the projection length can be shortened when the gas sensor is attached to the attachment object body 300.

Further, in the case of the third embodiment, the second terminal sections 31b2 and 32b2 directly communicate with the opening 63b of the connector section 63 and are electrically connected from the rear side by welding or the like to the connection terminals 31 and 32. Thus, the connection terminal 70 as in the first embodiment is not required so that productivity can be enhanced and the electrical connection from the gas sensor element 10 to the connector section 63 can be reliably accomplished.

Next, a configuration of a gas sensor 230 according to a fourth embodiment of the invention will be described with reference to FIG. 9. The configuration is the same as the first embodiment except that the gas sensor 230 has connection terminals 34 and 35 and a connection terminal 73, instead of the connection terminals 31 and 32 and the connection terminal 70 in the first embodiment, so that the same configuration portions as the first embodiment are given the same reference numbers and thus are not specifically described here.

Figure 9:
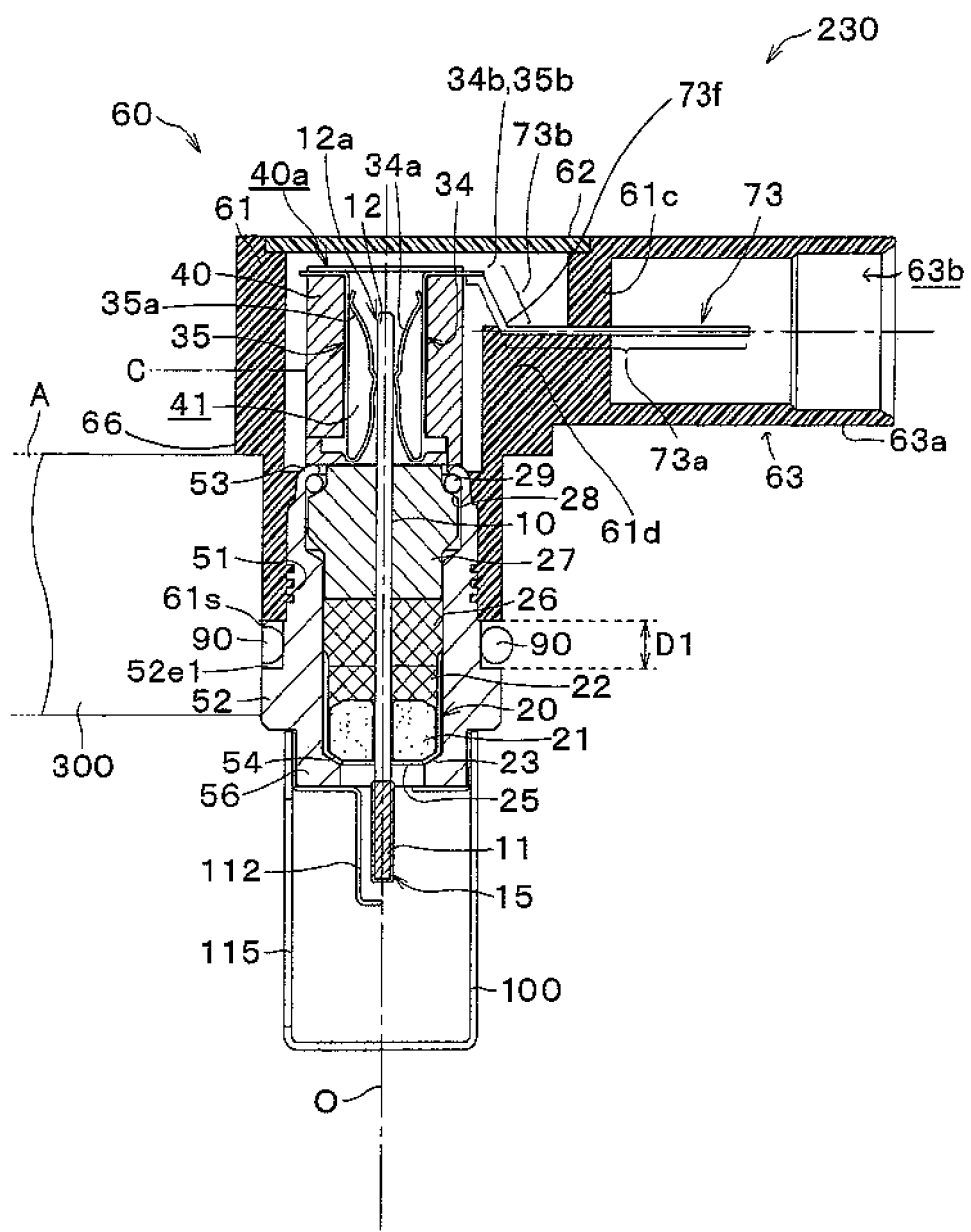
FIG. 9 is a cross sectional view illustrating a configuration of a gas sensor according to a fourth embodiment of the invention.

FIG. 9 is a cross sectional view illustrating a configuration of the gas sensor 230 and is a drawing corresponding to FIG. 2 of the first embodiment. In the drawing, the connection terminals 34 and 35 have element side sections 34a and 35a, and the external circuit side sections 34b and 35b the same as in the first embodiment. The external circuit side sections 34b and 35b have only horizontal sections (both are not shown) different from the first embodiment. Thus, the external circuit side sections 34b and 35b do not extend to the center of the separator 40 in the axial direction, but rather extend to outside with the same height as the upper surface 40a of the separator 40.

Also, a connector terminal 73 has a first connector terminal section 73a and a second connector terminal section 73b. The first connector terminal section 73a is accommodated in the connector section 63 and extends in the diametrical direction, and the second connector terminal section 73b extends and is tilted to the rear-end side (the upper surface 40a) of the separator 40 through a fourth bending section 73f from the first connector terminal section 73a.

Accordingly, the same as in the first embodiment, the separator 40 having mounted thereon the connection terminals 34 and 35 is inserted into the gas sensor element 10, and the external circuit side sections 34b and 35b are contacted to the terminal front-end of the second connector terminal section 73b. Thus, in this state, the terminal front-ends of the external circuit side sections 34b and 35b are electrically connected by welding or the like to a second connector terminal section 73b, respectively.

Even in the fourth embodiment, since the external circuit side sections 34b and 35b of the connection terminals 34 and 35 extend further to the outside in the diametrical direction than the outside surface of the separator 40, the height of the external circuit side sections 34b and 35b is lowered and the connector terminal 73 that is connected thereto does not project in the rear-end side further than the upper surface 40a of the separator 40. Accordingly, the height of the gas sensor in the axial direction O can be lowered as much, and the projection length can be shortened when the gas sensor is attached to the attachment object body 300.

Furthermore, in the fourth embodiment, since the second connector terminal section 73b is provided as part of the connection terminal 73 that is relatively thick and has high stiffness, when the second connector terminal section 73b contacts the external circuit side sections 34b and 35b, an elastic force of the second connector terminal section 73b is also increased and a connection pressure therebetween them is also increased, by the elastic force so that the reliability of the electric connection is enhanced. Also, in a case where the connection terminal extends in the diametrical direction from the lower surface 40b of the separator 40 different from the fourth embodiment, an extension of the second connector terminal section that connects to the connection terminal is preferably tilted so as to be lowered to the lower surface 40b of the separator 40.

The present invention is not limited to the above-described embodiments, and various modifications and changes may be made within the spirit and the scope of the claims appended hereto.

For example, the connector section need not be integrally mounted to the gas sensor, and the outer connector may be connected to the gas sensor through a conductive member such as a lead wire or terminal. Also, the conductive member may have a configuration such that a portion thereof is accommodated within the cover. Also, the material of the cover is not limited to a resin, and a portion of the cover may be made of a metal if the conductive member that is accommodated within the cover is insulated.

This application claims priority from Japanese Patent Application No. 2010-008503, which was filed on Jan. 18, 2010, the disclosure of which is incorporated herein by reference in its entirety.

What is claimed is:

1. A gas sensor comprising:
a gas sensor element that extends in an axial direction and has a detection section that detects a specific gas component in a measured gas at a front-end side thereof, and a plurality of electrode pads at a rear-end side thereof;
a plurality of connection terminals that are electrically connected to the plurality of electrode pads, respectively; and
an insulated separator that extends along the axial direction and has an inserting hole into which the plurality of connection terminals are inserted,
wherein the plurality of connection terminals have a plurality of element side sections that are arranged within the inserting hole and respectively connect to the plurality of electrode pads, and a plurality of external circuit side sections that extend further to the outside in a diametrical direction than an outer surface of the separator through one or more first bending sections from the plurality of element side sections,
wherein the gas sensor includes a connector section having an opening that is capable of connecting in the diametrical direction,
wherein respective ones of the plurality of external circuit side sections integrally have a first terminal section that extends toward the axial center of the separator through a second bending section that is arranged further to the outside in the diametrical direction than the outer surface of the separator, and a second terminal section that extends to the outside in the diametrical direction through a third bending section from the first terminal section, and
wherein the second terminal section is inserted through the opening of the connector section.

2. The gas sensor according to claim 1,
wherein the gas sensor includes a cover that covers the separator, and the connector section is an integral part of the cover.

3. The gas sensor according to claim 1,
wherein the rear-end side of the gas sensor element is inserted within the inserting hole of the separator, and respective ones of the plurality of element side sections of the plurality of connection terminals are slidably connected to the plurality of electrode pads of the gas sensor element that are accommodated in the inserting hole.

4. The gas sensor according to claim 1,
wherein the gas sensor element has a rectangular shape,
the plurality of electrode pads are arranged on a first surface of the gas sensor element that faces the connector section and on a second surface of the gas sensor element that is opposite the first surface, and
respective ones of the plurality of external circuit side sections of the plurality of connection terminals that are connected to the electrode pads formed on the second surface are arranged further outside of the connector section in the diametrical direction than the plurality of external circuit side sections of the connection terminal that are connected to the electrode pads formed on the first surface.

5. The gas sensor according to claim 1,
wherein the gas sensor element has a rectangular shape,
the plurality of electrode pads are arranged on a first surface of the gas sensor element that faces the connector section and on a second surface of the gas sensor element that is opposite the first surface, and
one of the plurality of external circuit side sections of the plurality of connection terminals that are connected to the electrode pads formed on the second surface and one of the plurality of external circuit side sections of the plurality of connection terminals that is connected to the electrode pads formed on the first surface is arranged to the rear of the separator and the other is arranged to the front of the separator.

6. A gas sensor comprising:
a gas sensor element that extends in an axial direction and has a detection section that detects a specific gas component in a measured gas at a front-end side thereof, and a plurality of electrode pads at a rear-end side thereof;
a plurality of connection terminals that are electrically connected to the plurality of electrode pads, respectively; and
an insulated separator that extends along the axial direction and has an inserting hole into which the plurality of connection terminals are inserted,
wherein the plurality of connection terminals have a plurality of element side sections that are arranged within the inserting hole and respectively connect to the plurality of electrode pads, and a plurality of external circuit side sections that extend further to the outside in a diametrical direction than an outer surface of the separator through one or more first bending sections from the plurality of element side sections,
wherein the gas sensor includes a connector section having an opening that is capable of connecting in the diametrical direction,
wherein respective ones of the plurality of external circuit side sections integrally have a first terminal section that extends toward the axial center of the separator through a second bending section that is arranged further to the outside in the diametrical direction than the outer surface of the separator, and a second terminal section that extends to the outside in the diametrical direction through a third bending section from the first terminal section, and
wherein the second terminal section is electrically connected to a connector terminal that is inserted through the opening of the connector section in the diametrical direction.

7. A gas sensor comprising:
a gas sensor element that extends in an axial direction and has a detection section that detects a specific gas component in a measured gas at a front-end side thereof, and a plurality of electrode pads at a rear-end side thereof;
a plurality of connection terminals that are electrically connected to the plurality of electrode pads, respectively; and
an insulated separator that extends along the axial direction and has an inserting hole into which the plurality of connection terminals are inserted,
wherein the plurality of connection terminals have a plurality of element side sections that are arranged within the inserting hole and respectively connect to the plurality of electrode pads, and a plurality of external circuit side sections that extend further to the outside in a diametrical direction than an outer surface of the separator through one or more first bending sections from the plurality of element side sections,
wherein the gas sensor includes a connector section having an opening that is capable of connecting in the diametrical direction,
wherein a plurality of connector terminals is inserted through the opening of the connector section,
each of the plurality of connector terminals includes a first connector terminal section that is inserted through the opening of the connector section in the diametrical direction, and a second connector terminal section that extends to the front-end side and/or the rear-end side of the separator in the axial direction through a fourth bending section from the first connector terminal section, and
each of the second connector terminal sections is electrically connected to one of the plurality of external circuit side sections.

* * * * *